US00PP31008P3

(12) United States Plant Patent
Warren

(10) Patent No.: US PP31,008 P3
(45) Date of Patent: Nov. 5, 2019

(54) CRABAPPLE TREE NAMED 'JFS KW213MX'

(50) Latin Name: *Malus*
Varietal Denomination: JFS KW213MX

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 15/932,167

(22) Filed: Feb. 14, 2018

(65) Prior Publication Data

US 2019/0254207 P1 Aug. 15, 2019

(51) Int. Cl.
*A01H 5/08* (2018.01)
*A01H 6/74* (2018.01)

(52) U.S. Cl.
USPC ..... Plt./173
CPC ..... *A01H 6/7418* (2018.05)

(58) Field of Classification Search
USPC ..... Plt./173
CPC ..... A01H 6/74; A01H 5/08
See application file for complete search history.

*Primary Examiner* — Keith O. Robinson
(74) *Attorney, Agent, or Firm* — Klarquist Sparkman, LLP

(57) ABSTRACT

A variety of crabapple which combines a combination of a narrow, upright columnar growth habit, short internodes resulting in compact growth, attractive reddish purple flowers, glossy reddish purple foliage, persistent fruit, and a strong resistance to the diseases fireblight and apple scab.

10 Drawing Sheets

Latin name of the genus and species of the plant claimed: *Malus*.

Variety denomination: 'JFS KW213MX'.

BACKGROUND OF THE INVENTION

In the fall of 1999, I collected open pollinated fruit from 21 experimental crabapple seedling trees, none of which were patented or introduced, and all of which have been subsequently destroyed. I extracted seed from these fruits and sowed the seed into seedbeds in a nursery in Boring, Oreg. I grew the resulting seedlings during the summer of 2000, then dug and transplanted them into a bed on wider spacing in the spring of 2001. During the late spring and summer of 2001, I inoculated these seedlings with apple scab fungus and I marked all seedlings showing infection for destruction. From this transplant bed, I kept and transplanted 1015 seedling trees that showed a degree of resistance to apple scab. During the summer of 2003, I selected a compact, upright, green-leafed tree that demonstrated moderately strong resistance to apple scab and I named it 'KW-78MX' (unpatented). I transplanted the 'KW-78MX' into an evaluation block in March of 2004. I evaluated 'KW-78MX' over the next two years and decided that, while its upright form was important for future breeding and selection, it was not good enough for introduction because its white flowers were slightly small compared to existing commercial cultivars and its fruits were too large for landscape use. All of these trees were grown in the same Boring, Oreg. nursery.

In the fall of 2006, I collected open pollinated fruit from the 'KW-78MX' tree. From these, I extracted seed and sowed the seed in beds. I obtained 273 seedlings generated from the seed from the 'KW-78MX' tree. I transplanted these seedlings on wider spacing in a nursery bed in the spring of 2008, inoculated these seedlings with apple scab and evaluated them for disease resistance. From this bed, I kept 33 open pollinated seedling trees from the seed from the 'KW-78MX' tree that showed resistance to apple scab and healthy foliage and I destroyed the others. These 33 seedling trees were planted in April of 2009 on wider spacing in a nursery row for further evaluation. During the summer of 2011, I selected five trees from these 33 open pollinated seedlings with unusually columnar growth habits. In the spring of 2012, I transplanted these five trees to a long term evaluation block and destroyed the other 28.

Of these five trees, one, which I named 'JFS KW213MX', possessed an outstanding and unique combination of a strongly columnar habit, reddish purple foliage, reddish purple flowers, relatively small, persistent fruit, and strong resistance to apple scab and fireblight diseases. The 'JFS KW213MX' tree is the subject of this description. Of the other four trees, three have been rejected in the selection process for disease susceptibility and inferior foliage quality, but have been retained in the row for possible future breeding. One additional tree of these five columnar selections has been named 'JFS KW214MX' and is the subject of U.S. Plant patent application Ser. No. 15/932,166. All of the above trees were grown and selected in the same Boring, Oreg. nursery. 'JFS KW214MX' has white flowers unlike the reddish purple flowers of 'JFS KW213MX'.

In the summers of 2011, 2012, and 2013, I collected propagating wood from the original 'JFS KW213MX' tree and directed asexual propagation by budding onto *Malus* rootstock in small experimental plots in a Canby, Oreg. nursery. This propagation resulted in 8, 6, and 9 trees, respectively. I evaluated these propagated trees in subsequent years and determined that these asexually propagated trees show that the characteristics of my new tree are firmly fixed and identical to my original tree in every manner that has been observed. Of these propagated trees, all were destroyed after evaluation except for one that was budded in 2011 and planted in the same Boring, Oreg. evaluation block as the original tree; and nine that were budded in 2013 and were planted in a scion orchard in the Canby, Oreg. nursery as a source for future asexual propagation.

BRIEF SUMMARY OF THE INVENTION

This new cultivar possesses a unique combination of characteristics that have proven firmly fixed in asexually propagated progeny and that comprise a combination of a narrow, upright columnar growth habit, short internodes resulting in compact growth, attractive reddish purple flowers, glossy reddish purple foliage, persistent fruit, and strong resistance to the diseases fireblight and apple scab.

BRIEF DESCRIPTION OF THE DRAWING

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
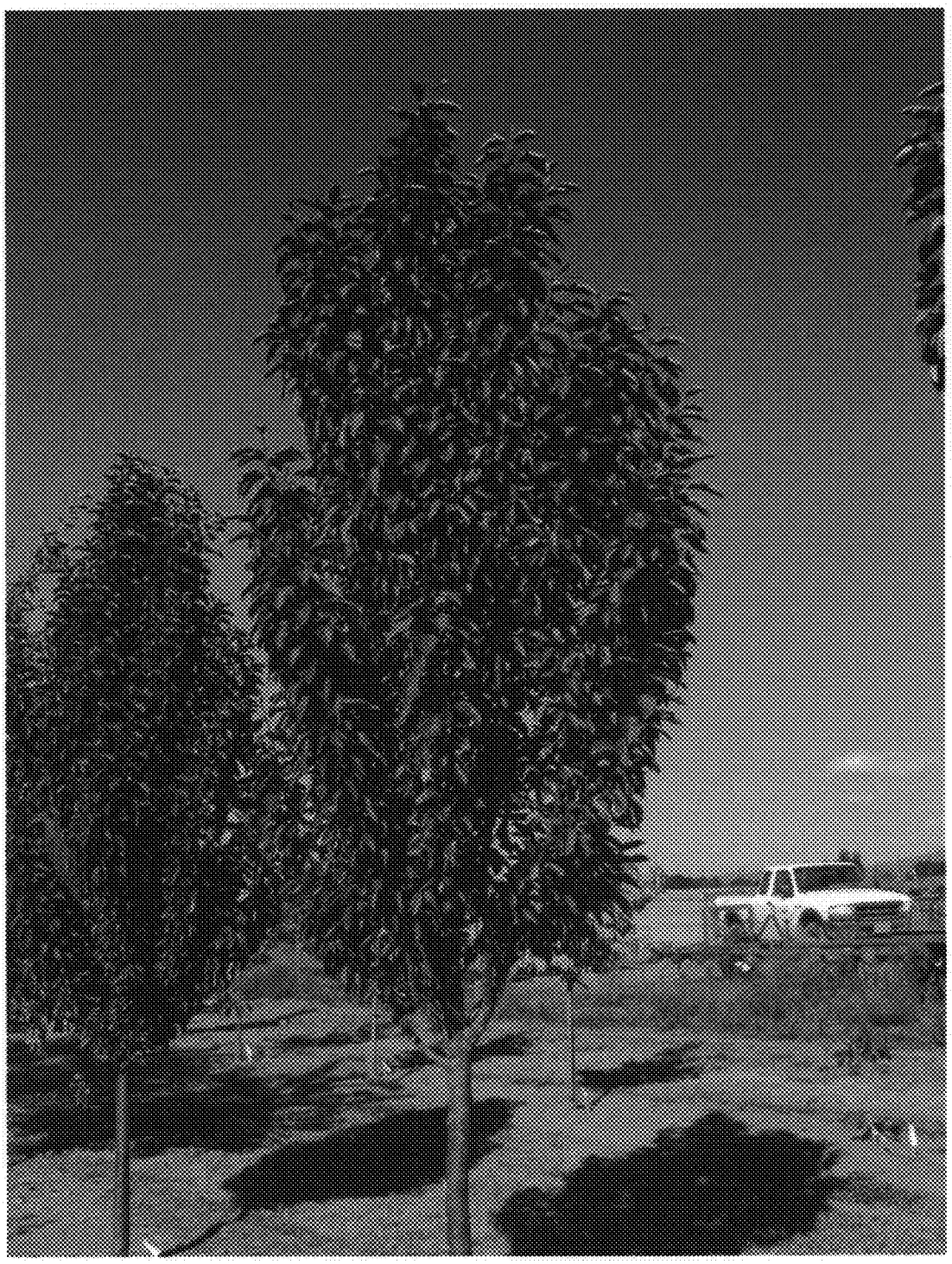
FIG. 1: Shows the original tree at 7 years old with summer foliage illustrating its narrow upright columnar shape
Figure 2:
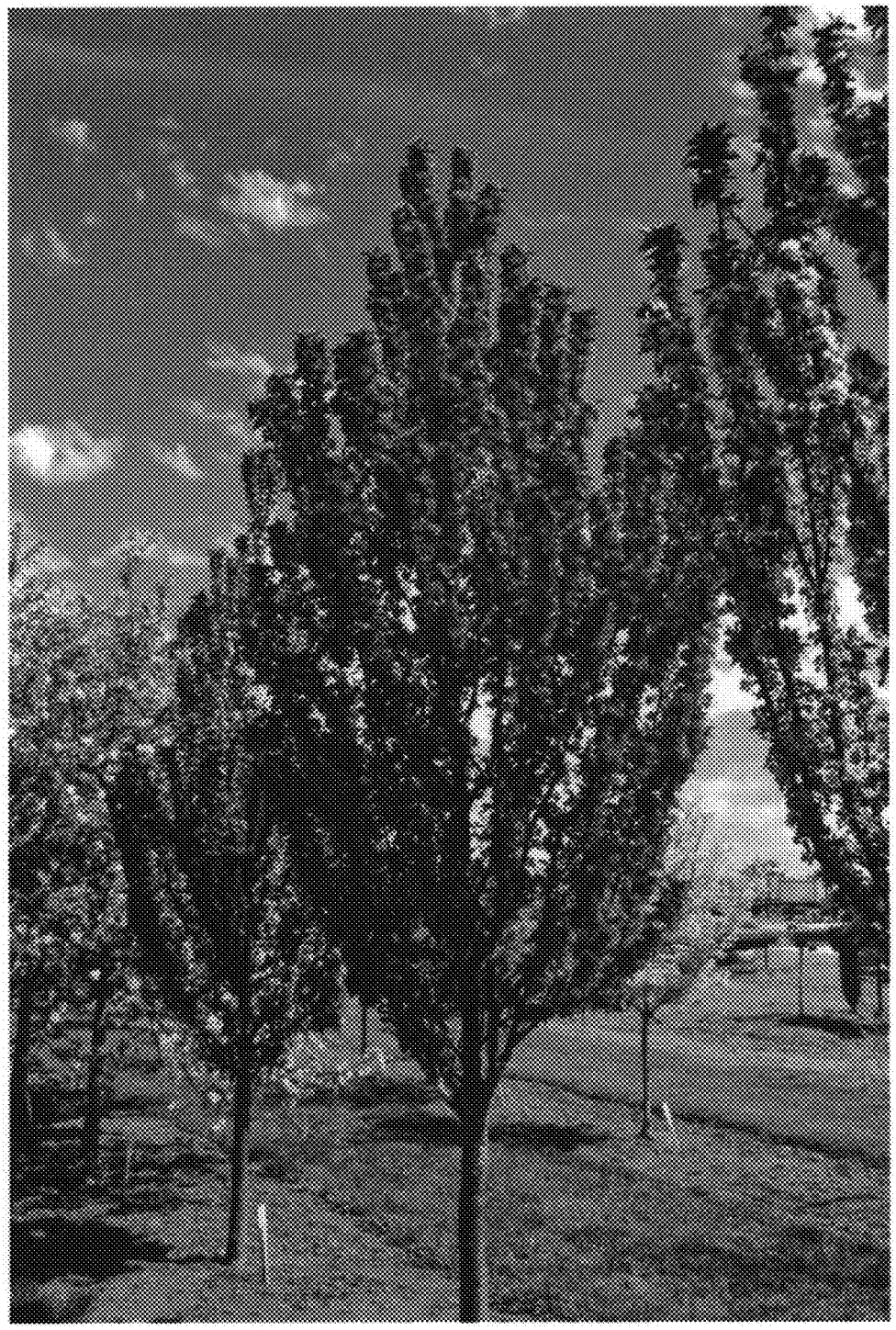
FIG. 2: Shows the original tree in flower at 10 years of age.
Figure 3:
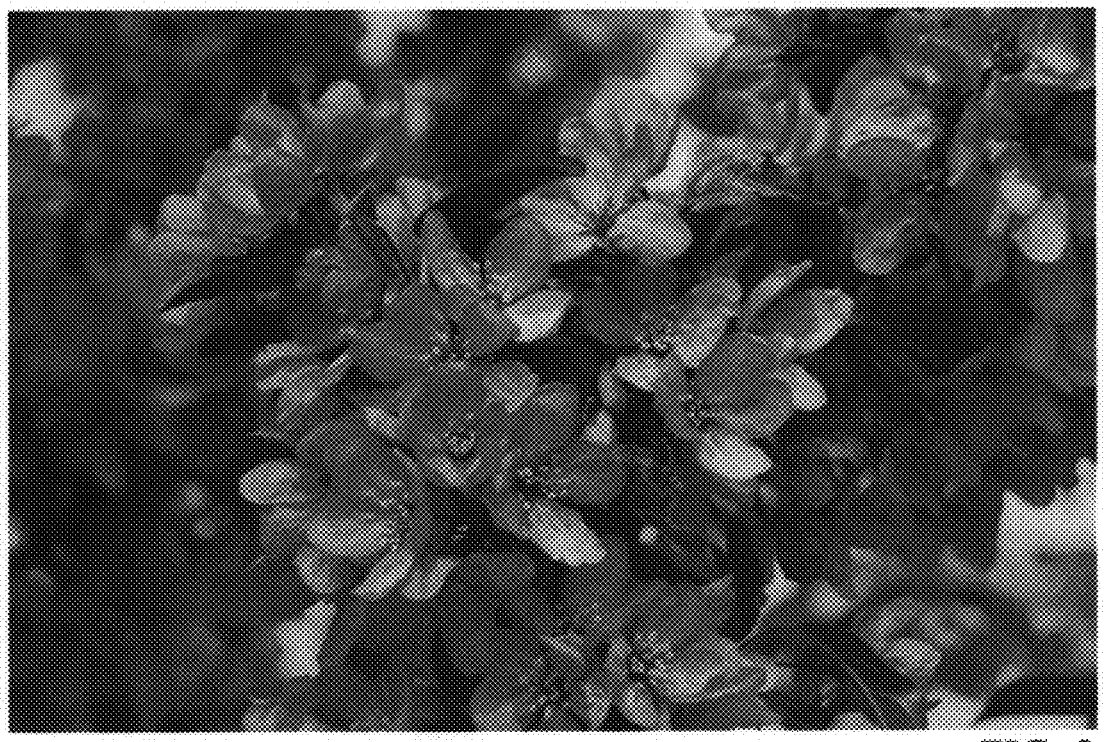
FIG. 3: Shows a close-up of the flowers on the original tree.
Figure 4:
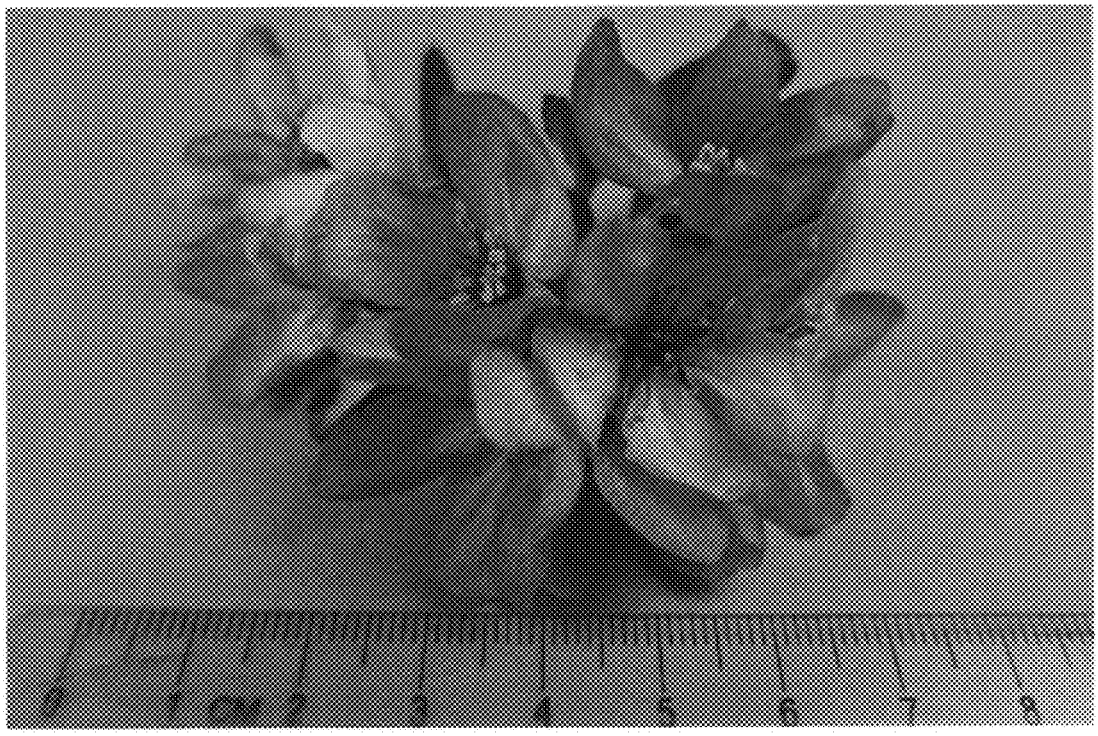
FIG. 4: Shows a close up of a few flowers on a display board with a scale.
Figure 5:
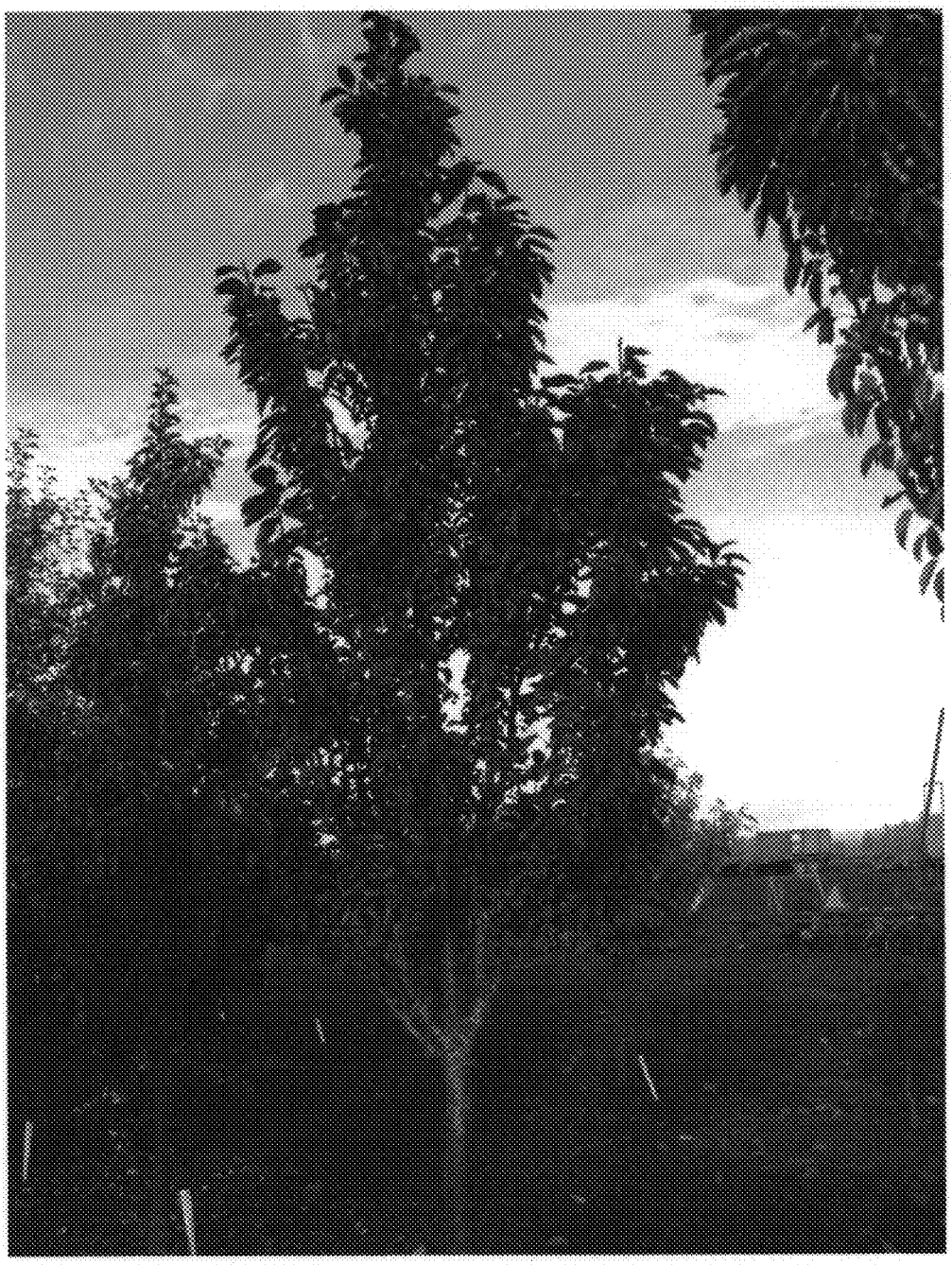
FIG. 5: Shows the original tree at 8 years of age with fruit
Figure 6:
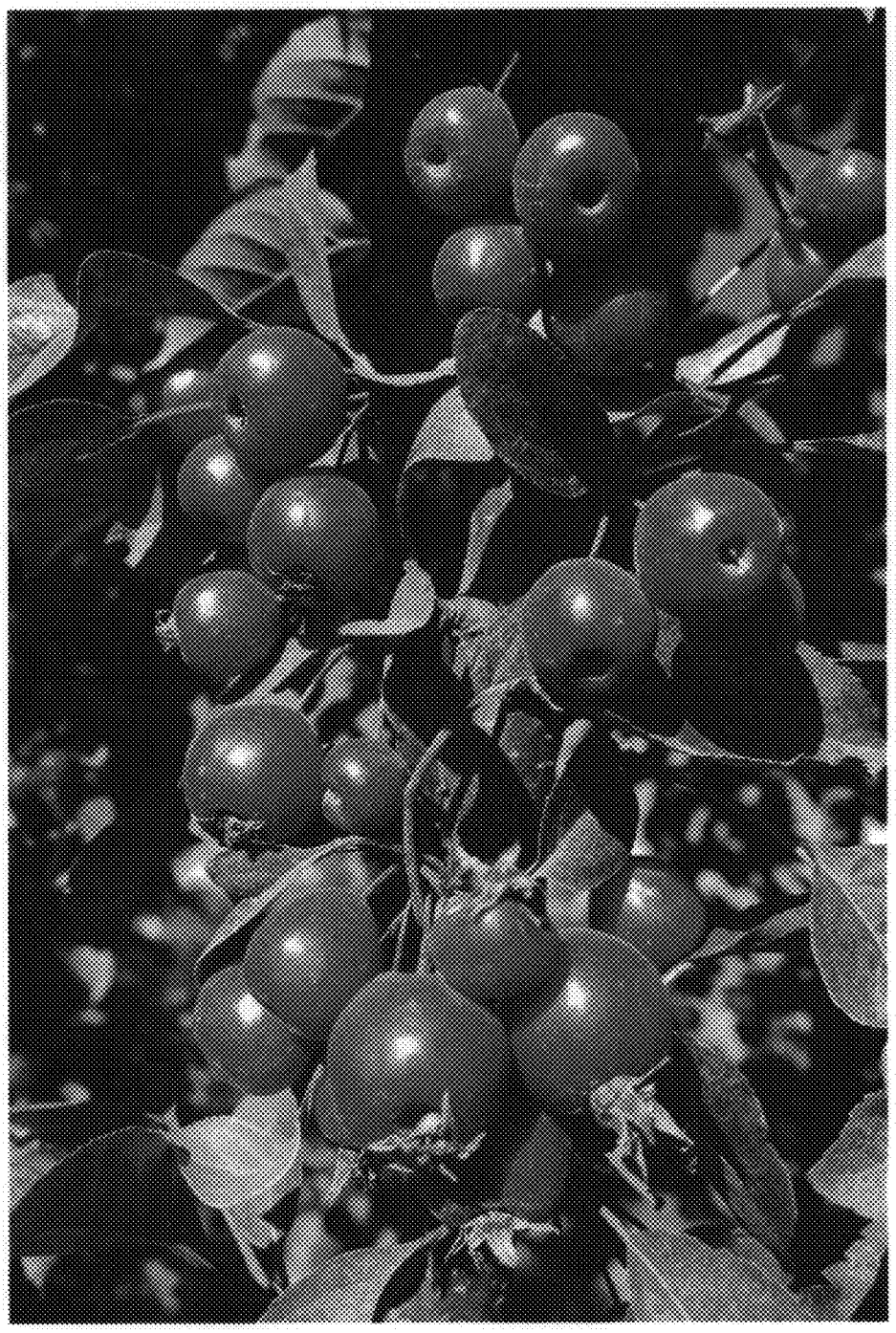
FIG. 6: Shows a close-up of the fruit on the original tree
Figure 7:
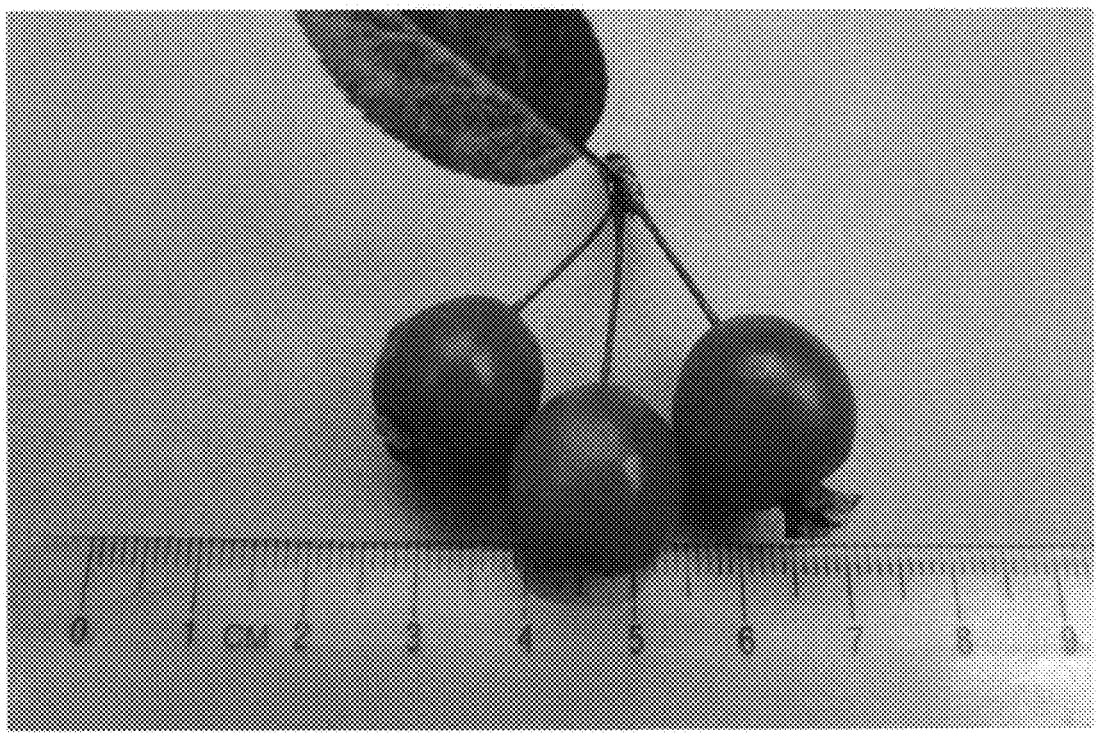
FIG. 7: Shows a close-up of fruit on a display board with a scale.
Figure 8:
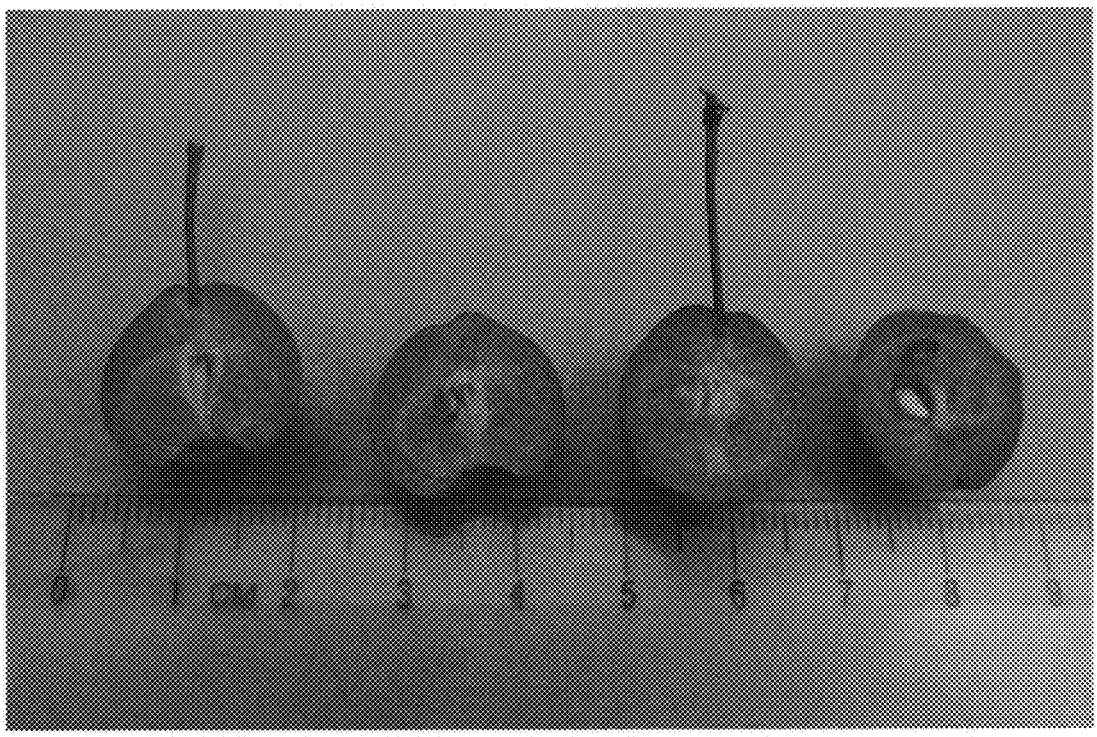
FIG. 8: Shows a close-up of fruit halved on a display board with a scale.
Figure 9:
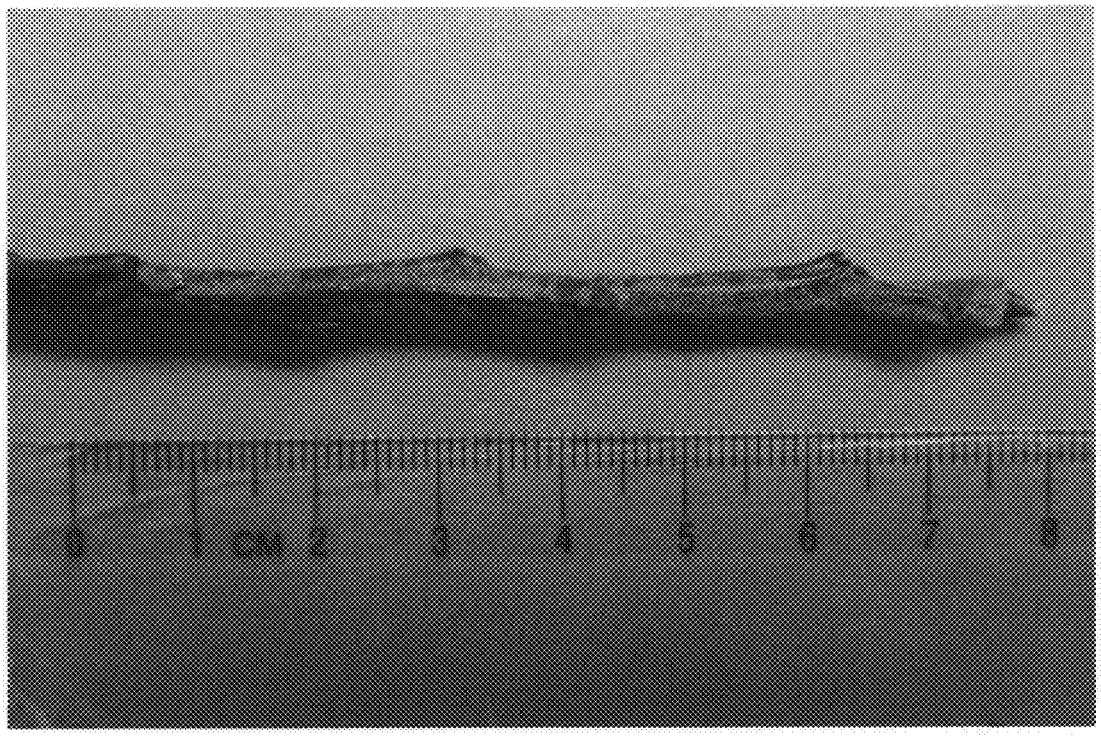
FIG. 9: Shows a dormant branch tip on a display board with a scale illustrating the short internode length.
Figure 10:
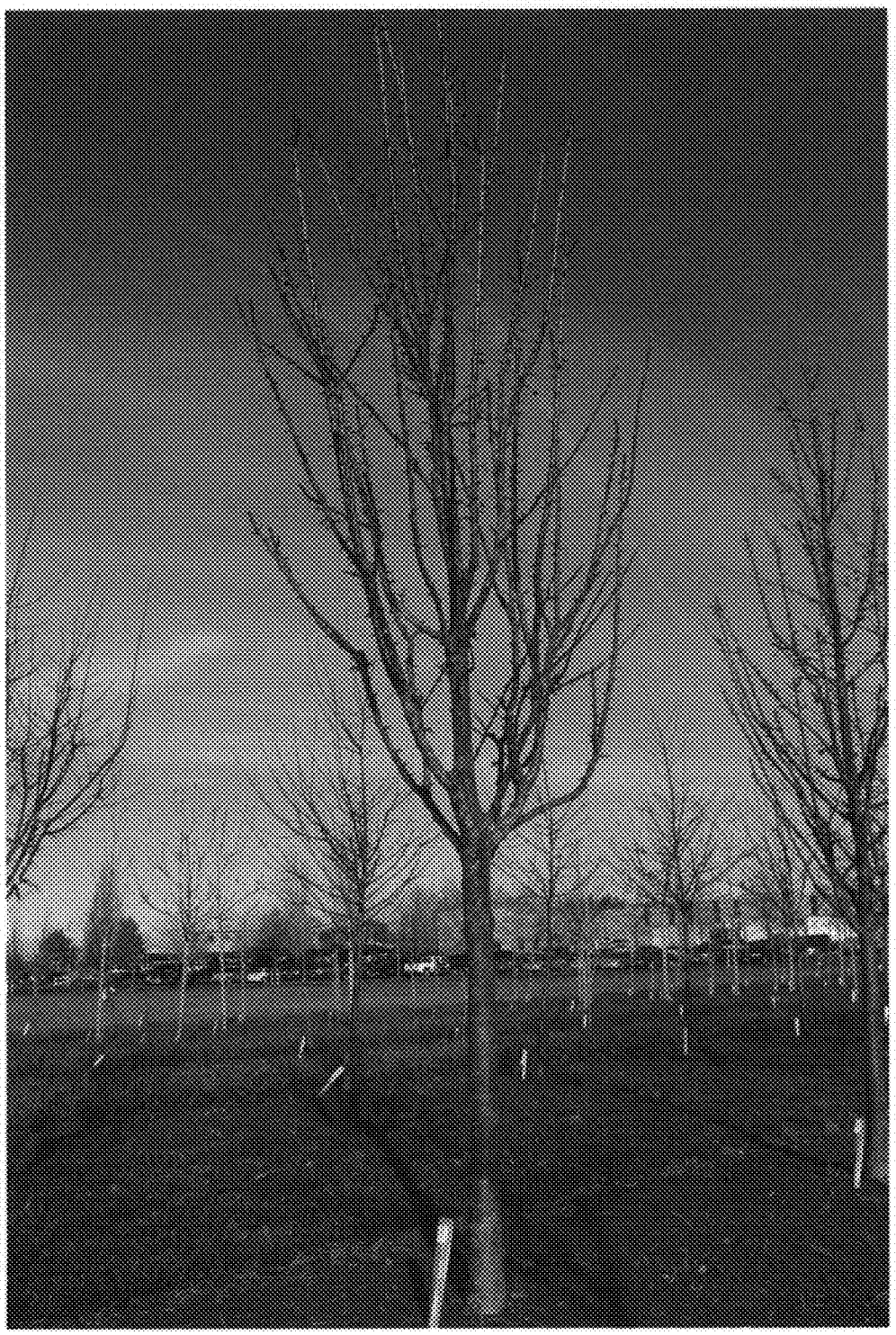
FIG. 10: Shows the original tree at 7 years of age without foliage during the winter illustrating its narrow upright columnar shape.

The following detailed description of the 'JFS KW213' variety is based on observations of the original tree growing in Boring, Oreg. and of two and three year old asexually reproduced progeny. The observed progeny were trees which were growing in Canby, Oreg. Color descriptions are made with reference to The Royal Horticultural Society (London) Colour Chart 1986, except where ordinary dictionary significance of color is indicated.

Scientific name: *Malus* 'JFS KW213MX'.

Parentage:

*Seed parent*.—Open pollinated seedlings of *Malus* 'KW-78MX'.

*Pollen parent*.—Unknown.

Tree:

*Overall shape*.—Narrow, upright column.

*Height*.—Original tree at 10 years of age, about 4.5 meters high.

*Width*.—Original tree at 10 years of age 1.70 meters spread.

*Caliper* (*trunk diameter*).—Original tree at 10 years of age, about 109 mm at 100 mm height, 88 mm at 800 mm height.

*Trunk*.—Strong and straight under nursery growing conditions.

*Trunk bark texture*.—Smooth, some vertical fissures with age.

*Trunk bark color*.—Brown 200A to Brown 200C.

*Immature bark color*.—Red Purple 72A to Red Purple 73A.

*Mature bark color*.—Purple 79A to 79C.

*Lenticels*.—Elongated 0.75 mm×0.25 mm disappearing by the 3$^{rd}$ year. Orange White 159C in color.

*Branch color*.—Purple 79A to Violet 83A.

*Branch lenticels*.—Similar to those on the trunk.

*Dormant buds*.—Elongated oval with acute tip, imbricate scales, 2 mm by 4 mm.

*Internodes*.—Average internode length is about 15-20 mm on a one-year old shoot.

*Hardiness*.—Has tolerated temperatures to 10 degrees F. in Boring Oreg. which is the lowest temperature experienced in this location. It is believed to have zone 4 cold hardiness similar to other plants of the same species.

*Disease resistance*.—Excellent resistance to fireblight (*Erwinia amylovora*), powdery mildew (*Podosphaera leucotricha*) & apple scab (*Venturia inaequalis*) on foliage and fruit.

Leaves: Except as otherwise noted, observations are from twenty vigorous growth leaves.

*Arrangement*.—Alternate.

*Type*.—Simple, entire, occasionally with 1 to 2 small lobes.

*Texture*.—Smooth, slight undulation between the veins.

*Sheen*.—Glossy on upper leaf surface only.

*Length*.—Averaging 70 mm to 90 mm.

*Width*.—Averaging 40 mm to 50 mm.

*Petioles*.—20 mm-30 mm long, about 1 mm in diameter.

*Overall shape*.—Ovate with 1 or 2 occasional side lobes.

*Margin*.—Serrulate.

*Tip*.—Acute.

*Base*.—Broadly acute.

*Stipules*.—Two per leaf, 10 mm to 15 mm long by 2 mm to 4 mm wide.

*Summer leaf color*.—Upper leaf surface: Red Purple 59A to Purple 79B. Lower leaf surface: Greyed Purple 183B to Greyed Purple 185A. Vein: Red Purple 61A to Purple 79A.

*Fall leaf color*.—Beginning Orange Red 35A turning to Orange Red 32A.

*Fall color begins*.—November 1$^{st}$ (Boring, Oreg. 2017).

*Fall color peak*.—November 15$^{th}$ (Boring, Oreg. 2017).

*Fall color ends*.—November 30$^{th}$ (Boring, Oreg. 2017).

*Pubescence*.—None.

*Persistence*.—Tree is deciduous.

Flowers:

*Overall*.—Number of flowers per cluster: 5 to 6; flowers are single.

*Shape*.—Symmetrical, rounded, 5 petals, cupped.

*Size*.—Approximately 30 mm to 34 mm in diameter.

*Unopened bud*.—Red Purple 60B to Red Purple 60C.

*Petals*.—Five petals per flower, 8 mm to 10 mm wide×16 to 18 mm long. Red Purple 61B fading to Red Purple 62C. Shape oval to obovate, petal margins are touching.

*Sepals*.—Acute, length 2 mm×6 mm at base. Red Purple 59B to 60A.

*Stamen*.—About fifteen to twenty stamens, 8 mm to 10 mm arranged concentrically around pistil. Red Purple 61A.

*Anthers*.—Greyed Orange 163A. 1 to 1.5 mm long by 0.5 mm to 0.25 mm in diameter.

*Pistil*.—Red Purple 61A compound, 3 to 5 branched, length 8 mm-10 mm. Ovary inferior, typically five carpels.

*Pollen*.—Yellow Orange 22B to 22C. Moderate amount of pollen.

*Pedicel*.—22 mm to 26 mm long by 0.5 mm to 0.6 mm in diameter. Red Purple 60D.

*Pubescence*.—Yes on the upper side of the sepal.

*Fragrance*.—Slightly sweet.

*Flowering date*.—In Boring, Oreg. 2017. First bloom April 16th, peak bloom April 22nd, last bloom May 7th. (Bloom was about 2 weeks later than average at this location in 2017 due to cold spring weather).

Fruit: Observations are from a sampling of typical fruit.

*Cluster*.—3 to 6 fruits per cluster.

*Size*.—Typical fruit is 15 mm to 17 mm in diameter by 16 mm to 18 mm long.

*Shape*.—Round to slightly oval.

*Skin*.—Smooth.

*Lenticels*.—None observed.

*Calyx*.—Sometimes present at maturity.

*Color*.—Immature summer fruit is Yellow Green 143C ripening to Red 44A in October; then turns Red 46A to Red 45B when fully ripe in October.

*Seeds*.—Typically 3 per fruit, ovoid, about 4 mm long and about 3 mm wide with a smooth surface, Greyed Orange 166C to Greyed Orange 165B in color.

*Fruit production*.—Prolific.

*Fruit persistence*.—90% still persistent Nov. 15, 2017.

*Usage*.—Ornamental, non-edible.

COMPARISON TO THE SEED PARENT

Compared to the seed parent tree 'KW-78MX', my new cultivar, 'JFS KW213MX', has larger flowers which are Purple Red 61B to Purple Red 62C compared to white. In addition, my new cultivar has foliage with an upper leaf surface color of Red Purple 59A to Purple 79B compared to the green upper surface leaf color of 'KW-78MX'. 'JFS KW213MX' has fruit which is 15-17 mm in diameter while 'KW-78MX' has 20-25 mm diameter fruit. In addition, 'JFS KW213MX' is highly resistant to apple scab disease whereas 'KW-78MX' is only moderately resistant to this disease.

COMPARISON TO OTHER VARIETIES

| | Malus 'JFS KW213MX' | Malus 'Durleo' PP20167 | Malus 'JFS W214MX' |
|---|---|---|---|
| Form | Narrow upright column | Compact upright oval. | Narrow upright column |
| Leaf Length | 80 mm to 90 mm | 85 mm | 60 mm to 65 mm |
| Leaf Width | 40 mm to 50 mm | 43 mm | 40 mm to 45 mm |
| Petiole | 20 mm | 27 mm | 20-25 mm |
| Spring Upper Leaf Color | Red Purple 59A to Purple 79B | Green 143B | Green 131A to 131C |
| Branch Color | Purple 79A to 79C | Greyed Purple 183B | Greyed Green 197A to Greyed Green 197C |
| Bark on trunk | Smooth with vertical fissures | Bole like bumps | Smooth, some vertical fissures. |
| Branch Angles on 2 YR trees | 40-50 degrees | 60-70 degrees | 40-50 degrees |
| Fruit Color | Red 44A to Red 46A | Red Purple 59A | Red 45A to Red 34A |
| Fruit Size | 15 to 17 mm × 16-18 mm | 10 mm × 10 mm | 13 to 14 mm long × 14-18 mm wide |
| Fruit Shape | Round to slightly oval | Round | Round to slightly flattened |

COMPARISON OF AVERAGE INTERNODE LENGTH

When compared to other commercial ornamental crab apple varieties 'JFS KW213MX' has significantly shorter average internode lengths.

| Cultivar | Average internode length |
|---|---|
| Malus 'JFS KW213MX' | 15-20 mm |
| Malus 'JFS-KW5' (PP14,375) | 25-30 mm |
| Malus 'Perfect Purple' (unpatented) | 25-30 mm |
| Malus 'Spring Snow' (unpatented) | 30-35 mm |
| Malus 'Prairiefire' (unpatented) | 30-35 mm |
| Malus 'Profusion' (unpatented) | 25-30 mm |

I claim:

1. A new and distinct variety of crabapple tree, as herein illustrated and described.

* * * * *